US009848915B2

(12) United States Patent
Beger et al.

(10) Patent No.: US 9,848,915 B2
(45) Date of Patent: Dec. 26, 2017

(54) PEDICLE SCREW SYSTEM AND SPINAL STABILIZATION SYSTEM

(71) Applicant: Aesculap AG, Tuttlingen (DE)

(72) Inventors: Jens Beger, Tuttlingen (DE); Claudia Stoerk, Emmingen (DE); Stefan Gassner, Immendingen-Hattingen (DE); Sven Krüger, Trossingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/948,840

(22) Filed: Nov. 23, 2015

(65) Prior Publication Data
US 2016/0143667 A1    May 26, 2016

(30) Foreign Application Priority Data
Nov. 24, 2014   (DE) .................. 10 2014 117 175

(51) Int. Cl.
*A61B 17/70*    (2006.01)
(52) U.S. Cl.
CPC ........ *A61B 17/7037* (2013.01); *A61B 17/704* (2013.01); *A61B 17/7032* (2013.01); *A61B 17/7044* (2013.01); *A61B 17/7077* (2013.01)
(58) Field of Classification Search
CPC .................................. A61B 17/7037
See application file for complete search history.

(56) References Cited

U.S. PATENT DOCUMENTS

| | | | | |
|---|---|---|---|---|
| 4,047,524 A | * | 9/1977 | Hall ................... | A61B 17/7022 411/471 |
| 5,108,395 A | * | 4/1992 | Laurain ................ | A61B 17/70 606/71 |
| 5,306,275 A | * | 4/1994 | Bryan ................ | A61B 17/1757 606/250 |
| 5,620,443 A | * | 4/1997 | Gertzbein .......... | A61B 17/7041 606/250 |
| 5,735,853 A | * | 4/1998 | Olerud .............. | A61B 17/7059 606/289 |
| 5,843,082 A | * | 12/1998 | Yuan .................. | A61B 17/7044 606/250 |
| 5,849,004 A | * | 12/1998 | Bramlet ............. | A61B 17/0401 606/232 |
| 5,899,904 A | * | 5/1999 | Errico ................ | A61B 17/7032 606/256 |

(Continued)

FOREIGN PATENT DOCUMENTS

| | | |
|---|---|---|
| DE | 19848715 | 8/2000 |
| DE | 102006055599 | 6/2008 |

(Continued)

*Primary Examiner* — Ellen C Hammond
*Assistant Examiner* — Stuart S Bray
(74) *Attorney, Agent, or Firm* — RatnerPrestia

(57) ABSTRACT

A pedicle screw system and/or a spinal stabilization system includes a pedicle screw having a screw shaft with an external thread and having a screw head supported on the screw shaft in a ball-and-socket joint relationship therewith. The screw head includes a connecting element receptacle for a connecting element of a spinal stabilization system. The pedicle screw system further includes a bone alignment device and a coupling device for at least one of force-locking coupling and form-locking coupling of the bone alignment device and the screw shaft when in an alignment position.

21 Claims, 8 Drawing Sheets

(56) References Cited

U.S. PATENT DOCUMENTS

| | | | | |
|---|---|---|---|---|
| 5,947,969 A * | 9/1999 | Errico | A61B 17/7032 | 606/308 |
| 6,206,879 B1 * | 3/2001 | Marnay | A61B 17/7035 | 606/53 |
| 6,533,787 B1 * | 3/2003 | Lenke | A61B 17/7008 | 606/75 |
| 6,602,255 B1 * | 8/2003 | Campbell | A61B 17/8042 | 606/290 |
| 7,455,684 B2 * | 11/2008 | Gradel | A61B 17/7044 | 606/246 |
| 7,615,069 B2 | 11/2009 | Paul | | |
| 7,883,510 B2 * | 2/2011 | Kim | A61B 17/0642 | 606/75 |
| 7,951,172 B2 * | 5/2011 | Chao | A61B 17/7037 | 606/265 |
| 8,337,532 B1 * | 12/2012 | McLean | A61B 17/7011 | 606/250 |
| 8,414,616 B2 * | 4/2013 | Berrevoets | A61B 17/7044 | 606/250 |
| 8,728,131 B2 * | 5/2014 | Di Giacomo | A61B 17/809 | 606/297 |
| 9,060,815 B1 * | 6/2015 | Gustine | A61B 17/705 | |
| 9,517,089 B1 * | 12/2016 | Casey | A61B 17/7035 | |
| 2002/0058939 A1 * | 5/2002 | Wagner | A61B 17/7059 | 606/86 B |
| 2004/0019353 A1 * | 1/2004 | Freid | A61B 17/1728 | 606/915 |
| 2004/0087951 A1 * | 5/2004 | Khalili | A61B 17/7059 | 606/281 |
| 2004/0127896 A1 * | 7/2004 | Lombardo | A61B 17/8042 | 606/290 |
| 2004/0172022 A1 * | 9/2004 | Landry | A61B 17/1604 | 606/86 A |
| 2004/0181227 A1 * | 9/2004 | Khalili | A61B 17/7059 | 606/281 |
| 2005/0010219 A1 * | 1/2005 | Dalton | A61B 17/7059 | 606/287 |
| 2005/0027296 A1 * | 2/2005 | Thramann | A61B 17/7059 | 606/281 |
| 2005/0033298 A1 * | 2/2005 | Hawkes | A61B 17/7059 | 606/281 |
| 2005/0038432 A1 * | 2/2005 | Shaolian | A61B 17/1671 | 606/86 A |
| 2005/0049593 A1 * | 3/2005 | Duong | A61B 17/8047 | 606/287 |
| 2005/0059971 A1 * | 3/2005 | Michelson | A61B 17/1604 | 623/17.11 |
| 2005/0085813 A1 * | 4/2005 | Spitler | A61B 17/1757 | 606/86 A |
| 2005/0154392 A1 * | 7/2005 | Medoff | A61B 17/8047 | 606/287 |
| 2005/0192577 A1 * | 9/2005 | Mosca | A61B 17/1615 | 606/86 B |
| 2005/0277937 A1 * | 12/2005 | Leung | A61B 17/8057 | 606/287 |
| 2006/0009770 A1 * | 1/2006 | Speirs | A61B 17/8047 | 606/287 |
| 2006/0100626 A1 * | 5/2006 | Rathbun | A61B 17/1728 | 606/86 B |
| 2006/0122602 A1 * | 6/2006 | Konieczynski | A61B 17/7059 | 606/281 |
| 2006/0122604 A1 * | 6/2006 | Gorhan | A61B 17/8038 | 606/86 B |
| 2006/0149249 A1 * | 7/2006 | Mathoulin | A61B 17/1615 | 606/915 |
| 2008/0086131 A1 * | 4/2008 | Daly | A61B 17/7032 | 606/264 |
| 2009/0062914 A1 * | 3/2009 | Marino | A61B 17/7061 | 623/11.11 |
| 2009/0192553 A1 * | 7/2009 | Maguire | A61B 17/8038 | 606/305 |
| 2009/0270916 A1 * | 10/2009 | Ramsay | A61B 17/1735 | 606/246 |
| 2010/0305616 A1 | 12/2010 | Carbone | | |
| 2012/0071928 A1 * | 3/2012 | Jackson | A61B 17/7005 | 606/257 |
| 2013/0030474 A1 | 1/2013 | Chaput | | |
| 2013/0150904 A1 | 6/2013 | Biedermann | | |
| 2013/0204308 A1 | 8/2013 | Barry | | |
| 2015/0320468 A1 | 11/2015 | Kruger | | |

FOREIGN PATENT DOCUMENTS

| | | |
|---|---|---|
| DE | 102012219630 | 4/2014 |
| DE | 102013100574 | 7/2014 |
| FR | 2761876 | 10/1998 |
| WO | 2013134368 | 9/2013 |

* cited by examiner

PEDICLE SCREW SYSTEM AND SPINAL STABILIZATION SYSTEM

CROSS-REFERENCE TO RELATED APPLICATIONS

The present disclosure relates to and claims the benefit of priority of German patent application number 10 2014 117 175.6, filed Nov. 24, 2014, the content of which is incorporated by reference herein in its entirety and for all purposes.

FIELD

The present invention relates to pedicle screw systems generally, and more specifically to a pedicle screw system, comprising a pedicle screw having a screw shaft with an external thread and having a screw head supported on the screw shaft in a ball-and-socket joint relationship therewith, which screw head comprises a connecting element receptacle for a connecting element of a spinal stabilization system.

The invention further relates to spinal stabilization systems generally, and more specifically to a spinal stabilization system comprising at least two bone screws and at least one connecting element capable of being fixed in place on the at least two bone screws.

BACKGROUND

Pedicle screws and spinal stabilization systems of the type described at the outset are known for example from DE 10 2013 100 574 A1. They can be used for example in deformity surgery in order to impart to a deformed spine a desired form and fix it thereinto by appropriate implantation and alignment of pedicle screws. For the alignment of individual malpositioned vertebrae, the forces for the corrective maneuver are introduced into the respective vertebra via the pedicle screws.

In pedicle screw systems which permit top-loading of a connecting element into a corresponding connecting element receptacle on the screw head, i.e. in what are known as "tulip" design systems, an introduction of force is not possible if the pedicle screw is configured in the form of a polyaxial screw. Force introduction is only possible if the screw head is immovable relative to the screw shaft or is, at most, pivotable about a single axis, i.e. if the pedicle screw is what is known as a monoaxial screw. With this design, the screw head is moved in a plane which extends perpendicularly to the axis about which it is pivoted so that in this sense the monoaxial screw can also be referred to as a uniplanar screw. With polyaxial screws, on the other hand, which considerably simplify the insertion of the connecting element, such as a rod, by the screw head being able to be given any desired orientation with respect to the screw shaft, such an introduction of force and correction of a vertebra's alignment is not possible or is possible in only a rudimentary form. In particular, the technique of segmental derotation cannot be applied with polyaxial screws. This technique can only be implemented with the direct introduction of force into the pedicle screw as allowed by the described monoaxial screws in particular.

SUMMARY

In a first aspect of the invention, a pedicle screw system comprises a pedicle screw having a screw shaft with an external thread and having a screw head supported on the screw shaft in a ball-and-socket joint relationship therewith. Said screw head comprises a connecting element receptacle for a connecting element of a spinal stabilization system. Said pedicle screw system further comprises: a bone alignment device and a coupling device for at least one of force-locking coupling and form-locking coupling of the bone alignment device and the screw shaft when in an alignment position.

In a second aspect of the invention, a spinal stabilization system comprises at least two bone screws and at least one connecting element fixable on the at least two bone screws. At least one of the at least two bone screws is configured in the form of a pedicle screw system comprising a pedicle screw having a screw shaft with an external thread and having a screw head supported on the screw shaft in a ball-and-socket joint relationship therewith. Said screw head comprises a connecting element receptacle for a connecting element of a spinal stabilization system. Said pedicle screw system further comprises: a bone alignment device and a coupling device for at least one of force-locking coupling and form-locking coupling of the bone alignment device and the screw shaft when in an alignment position.

BRIEF DESCRIPTION OF THE DRAWING FIGURES

The foregoing summary and the following description may be better understood in conjunction with the drawing figures, of which:

DETAILED DESCRIPTION

Figure 1:
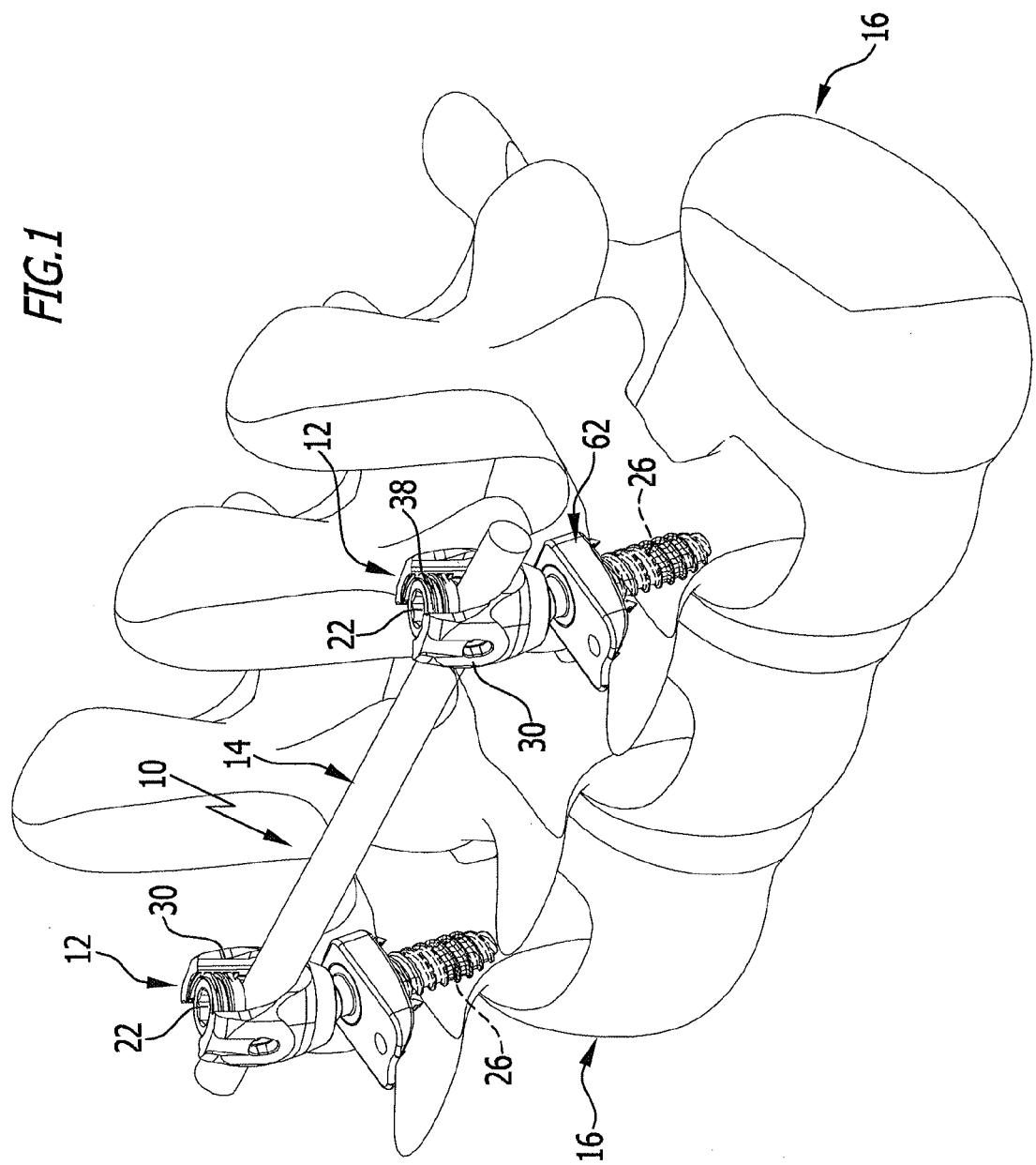
FIG. 1 is a schematic view of a spinal stabilization system comprising two bone screws and a connecting element, shown as being fixed in place on a spine.

Although the invention is illustrated and described herein with reference to specific embodiments, the invention is not intended to be limited to the details shown. Rather, various modifications may be made in the details within the scope and range of equivalents of the claims and without departing from the invention.

The invention relates to a pedicle screw system, comprising a pedicle screw having a screw shaft with an external thread and having a screw head supported on the screw shaft in a ball-and-socket joint relationship therewith, which screw head comprises a connecting element receptacle for a connecting element of a spinal stabilization system, said pedicle screw system further comprising: a bone alignment device and a coupling device for at least one of force-locking coupling and form-locking coupling of the bone alignment device and the screw shaft when in an alignment position.

In particular, the improvement proposed in accordance with the invention enables the surgeon to introduce forces for moving, in particular rotating, deformed vertebrae of a vertebral column via the bone alignment apparatus into the screw shaft directly when the coupling device of the pedicle screw system assumes the alignment position. The proposed pedicle screw system therefore combines, on the one hand, the advantages of polyaxial screws, which enable the screw head to be imparted any desired alignment relative to the screw shaft in order to facilitate insertion of the connecting element into the connecting element receptacle of the screw head, with, on the other hand, the advantages of rigid screws or monoaxial screws, which enable the introduction of forces to the screw shaft for aligning a vertebral body into which the pedicle is screw is screwed. In particular, the coupling device allows for an axial and/or a rotationally fixed connection to be established between the bone alignment device and the screw shaft, thereby enabling, via the bone alignment device, an indirect transfer of force from an alignment instrument to the screw shaft for example.

A particularly simple and economic configuration for the pedicle screw system can be obtained if the bone alignment device is configured in the form of a bone plate. In particular, the bone plate can have a bone contact face which enables as large a surface contact as possible with bone. In particular, it may be shaped or adapted in a manner corresponding to an anatomic curvature of the bone against which it is to be brought into contact. For example, a patient-individual curvature of the bone plate can be created on the basis of the patient's data, in particular CT data or other data generated by imaging techniques. Shaping of the in particular patient-individual bone plate can be done for example by material-removing machining processes, in particular milling, or by generative manufacturing processes, in particular laser sintering.

In order to prevent, or minimize the risk of, rotation of the bone alignment device on the bone against which it is in contact, it is advantageous for the bone alignment device to carry or comprise at least one bone anchoring element.

Advantageously, the at least one bone anchoring element is configured in the form of a bone pin or a bone tooth. In particular, these can be formed in projecting relationship to the bone alignment device configured in the form of a bone plate.

In order to make for a bone alignment device that is of particular stability, it is advantageous for the at least one bone anchoring element to be configured in one piece with the bone alignment device.

In accordance with another preferred embodiment of the invention, provision may be made for the coupling device to comprise first and second coupling elements which are in force-locking and/or form-locking engagement when in the alignment position and are arranged or formed on the bone alignment device on the one hand and the screw shaft on the other. With a coupling device configured in this way, it is easily possible to establish an axial and/or a rotationally fixed connection between the bone alignment device and the screw shaft, in particular when in the alignment position. Before the pedicle screw system assumes the alignment position, the first and second coupling elements can, depending on the concrete configuration thereof, be for example rotated to each other, in particular polyaxially rotated through the formation of a ball-and-socket joint between the first and the second coupling element, to then be fully or partially limited in their freedom of motion relative to each other. For example, with the pedicle screw threaded fully or almost fully into the bone, the first and second coupling elements forming a ball-and-socket joint can be pressed to each other or be actively blocked relative to one another by an additional blocking element.

It is advantageous for the first coupling element to be configured in the form of a coupling projection and for the second coupling element to be configured in the form of a coupling receptacle corresponding to the coupling projection. For example, the coupling projection can be formed on the bone alignment device or on the screw shaft. Accordingly, the coupling receptacle can be correspondingly formed on the screw shaft or on the bone alignment device.

An axial and/or a rotationally fixed connection between the bone alignment device and screw shaft can be realized in a simple manner by the coupling projection engaging in the coupling receptacle in a form-locking or essentially form-locking manner when in the alignment position.

Preferably, the coupling projection is configured in one piece with the screw shaft or is connected to the screw shaft in a force-locking manner and/or with a substance-to-substance bond. For example, the coupling projection can be connected to the screw shaft by press-fitting, adhesive bonding, soldering or welding. In particular, the coupling projection permits forces to be introduced, via the coupling projection, from the bone alignment device to the screw shaft.

The pedicle screw system can be manufactured with particular ease and economy if the coupling projection is configured in the form of an annular flange. This can be formed in one piece with the screw shaft, for example.

For the formation of a polyaxial screw, it is advantageous if the screw shaft has a joint head and if the screw head has a joint head receptacle corresponding to the joint head for forming a ball-and-socket joint in cooperation with the joint head. With such a configuration, it is in particular possible to rotate and align the screw head relative to the screw shaft about a midpoint of a for example spherical-shaped joint head.

In order to make for as compact a construction of the pedicle screw as possible, it is advantageous for the coupling projection to be arranged between the external thread and the joint head.

Preferably, an external diameter of the coupling projection is larger than a maximum external diameter of the external thread. In this way, it is in particular possible for the coupling projection to be also utilized as a stop element in order to achieve a defined coupling between the screw shaft and the bone alignment device.

Advantageously, the coupling projection is directly adjacent to the external thread. In this way, in particular, threading the screw shaft into bone as far as the coupling projection will permit can be accomplished even without the use of the bone alignment device.

It is advantageous for the coupling receptacle to be configured in the form of a recess of the bone alignment device. This provides a simple way of engaging the coupling projection of the screw shaft in the coupling receptacle.

Furthermore, provision may be made for the bone alignment device to comprise a screw shaft receptacle in which the screw shaft engages at least partially when in the alignment position. For example, the screw shaft can also extend through the screw shaft receptacle when in the alignment position. This provides a way of achieving additional optimization in the coupling between the bone alignment device and the screw shaft.

To allow the screw shaft to be easily introduced into the screw shaft receptacle, it is advantageous for the screw shaft receptacle to be configured in the form of a through-hole of the bone alignment device. For example, the through-hole can be configured in the form of a bore. Alternatively, it is also possible for the screw shaft receptacle to be configured with a cross-section that has n-fold symmetry. In particular, this provides a simple way of creating a rotationally fixed coupling between the bone alignment device and the screw shaft.

To make for a construction of the pedicle screw that is as compact as possible, it is advantageous for the coupling receptacle to be directly adjacent to the screw shaft receptacle. By appropriate shaping of the coupling receptacle and of the screw shaft receptacle, this then provides a simple way of creating both axial fixation and a rotationally fixed connection in a circumferential direction.

Preferably, the coupling receptacle has an internal diameter that is larger than that of the screw shaft receptacle. In this manner, the screw shaft receptacle can form a stop for the coupling projection when the latter engages into the coupling receptacle.

In accordance with another preferred embodiment of the invention, provision may be made for the coupling device to define a longitudinal axis which runs parallel to a screw shaft longitudinal axis of the screw shaft or encloses an angle of inclination therewith. For example, the bone alignment device can be configured in the form of a bone plate which defines a plane. Relative to said plane, it is then possible to achieve a coupling between the bone alignment device and the screw shaft in which the screw shaft longitudinal axis is aligned perpendicularly to or is inclined relative to the plane defined by the bone plate. For example, depending on the shape of a vertebra, bone alignment devices of differing configurations can be provided in the form of a set of bone alignment devices in order to provide a surgeon with an optimum selection of bone alignment devices to allow him or her to choose the best possible one for the particular patient in order to bring the deformed spine back into a desired form.

For example, in order to allow for a vertebra having a pedicle screw screwed in place therein to be aligned in a simple manner by use of an alignment instrument, it is advantageous for the bone alignment device to have at least one coupling device for temporary force-locking and/or form-locking coupling with an alignment instrument in a coupling position. That is, the coupling device enables a surgeon to bring an alignment instrument into engagement with the bone alignment device when required and thus, by use of the alignment instrument, to transfer a force for aligning the vertebral body, via the bone alignment device, to the screw shaft and hence to the vertebra.

To enable simple coupling with a wide variety of alignment instruments, it is advantageous for the at least one coupling element to be configured in the form of a coupling projection and/or in the form of a coupling recess. In particular, this also means that the at least one coupling element can be configured partially as a coupling projection and partially as a coupling recess. By way of example, an alignment instrument can engage with a free end thereof in a coupling recess or receive in a recess provided on its free end a coupling projection provided on the bone alignment device in order to preferably achieve an axial and/or a rotationally fixed coupling between the alignment instrument and the bone alignment device.

The coupling device is particularly simple to manufacture if the coupling recess is configured in the form of a blind hole or a through-hole. The through-hole can be configured in the form of a bore in particular.

To enable a defined connection between the bone alignment device and an alignment instrument, it is advantageous for the at least one coupling element to comprise a thread or to be configured in the form of a latch element. By way of example, the thread can be configured in the form of an external thread or in the form of an internal thread. This provides a simple way of threadingly engaging the alignment instrument with the bone alignment device. A simple form of the connection is achieved if the coupling element is configured in the form of a latch element so that the alignment instrument and the bone alignment device can be easily latched into mutual engagement in order to couple them in an axial and/or in a rotationally fixed relation to one another.

Advantageously, the pedicle screw system comprises an alignment instrument for temporary force-locking and/or form-locking coupling with the coupling device. By use of the alignment instrument, a force for aligning a vertebra can be exerted via the bone alignment device to the screw shaft in the manner described.

Preferably, the alignment instrument comprises on the distal side thereof a coupling end for force-locking and/or form-locking coupling with the coupling device. In particular, a coupling end configured in this manner provides a simple and safe way for the alignment instrument to be coupled with the bone alignment device in, for example, axial and/or rotationally fixed relation therewith.

In accordance with a particularly preferred embodiment of the invention, provision may be made for the coupling end to be configured in the form of a latch element or to comprise a thread which is of a configuration corresponding to that of the thread of the at least one coupling element. The coupling end in the form of a latch element can be brought into latching engagement with a correspondingly configured latch element on the bone alignment device in a simple manner in order to establish an axial and/or a rotationally fixed connection in a quick and simple manner. Alternatively, the threaded coupling end can be threadingly engaged with the thread of the at least one coupling element.

The present invention further relates to a spinal stabilization system, comprising at least two bone screws and at least one connecting element fixable on the at least two bone screws, wherein at least one of the at least two bone screws is configured in the form of a pedicle screw system comprising a pedicle screw having a screw shaft with an external thread and having a screw head supported on the screw shaft in a ball-and-socket joint relationship therewith, which screw head comprises a connecting element receptacle for a connecting element of a spinal stabilization system, said pedicle screw system further comprising: a bone alignment device and a coupling device for at least one of force-locking coupling and form-locking coupling of the bone alignment device and the screw shaft when in an alignment position.

In particular, such an improved spinal stabilization system then also includes the advantages described above in connection with preferred embodiments of pedicle screw systems.

FIG. 1 illustrates an example of a spinal stabilization system, designated generally by the reference character 10, said spinal stabilization system 10 comprising two bone screws 12 and a connecting element 14 fixed in place on the two bone screws 12. The bone screws 12 are each fixed in place on a vertebra 16 of a spine 18.

Of course, the spinal stabilization system 10 can also comprise more than two bone screws 12. These can be connected together via one or more connecting elements 14 for example.

FIG. 1 shows an example of a connecting element 14 which takes the form of a round rod. It is also conceivable for the connecting element 14 to take the form of plate-like connecting elements having appropriately configured sections that can be inserted into the connecting element receptacles of the bone screws and can, for example, be fixed in place by a fixation screw 22.

In principle, the bone screws 12 may be conventional pedicle screws available on the market. It is, however, preferred for at least one of the bone screws 12 to be configured in the form of a pedicle screw system 20 which will be described in detail below.

Each of the pedicle screw systems 20 comprises a pedicle screw 24 having a screw shaft 26 with an external thread 28, for example in the form of a self-tapping bone thread, and having a screw head 30 supported on the screw shaft 26 in a ball-and-socket joint relationship therewith. The screw head 30 has a connecting element receptacle 34 formed between two free legs 32 for receiving the connecting element 14 of the spinal stabilization system 10.

Furthermore, the connecting element receptacle 34 has provided thereon an internal thread 36 of a configuration corresponding to an external thread 38 of the fixation screw 22 so that the fixation screw for fixing in place the connecting element 14 can be screwed, starting from free ends of the legs 32, into the connecting element receptacle 34 in order to fix the connecting element 14 in place on the screw head 30.

To form a ball-and-socket joint 40 between the screw shaft 26 and the screw head 30, a proximal end of the screw shaft 26 is configured in the form of a joint head 42 having a planar end face 44 pointing in a proximal direction, said end face 44 having adjacent thereto a joint head face 46 forming part of a surface of a sphere. Pointing in a proximal direction, a tool element receptacle 48 is formed in the joint head 42, and this can take the form of for example an internal polygon or an internal polygon with rounded corners.

Formed on the screw head 30 is a joint head receptacle 50 in the form of a seat 52 having a configuration corresponding to the joint head 42, said seat 52 opening into a through-hole 54 tapering in internal diameter in a distal direction, said through-hole 54 being formed at a distal end 56 of the screw head 30 and having the screw shaft 26 protruding therefrom distally of the joint head 42.

On the distal side, the joint head 42 is adjoined by a non-threaded shaft section 58 which is bounded by an annular flange 60 on the distal side. The annular flange 60 has an external diameter that is somewhat larger than an external diameter of the joint head 42.

The pedicle screw system 20 further comprises a bone alignment device 62 and a coupling device 64 for force-locking and/or form-locking coupling of the bone alignment device 62 and the screw shaft 26 when in an alignment position as shown in FIGS. 1 to 6 for example.

The bone alignment device 62 is configured in the form of a bone plate 66 which has a planar upper side 68 and has a concavo-convexly curved underside 70 preferably adapted to a contour of a pedicle. Projecting from the underside of the bone alignment device 62 are a plurality of bone anchoring elements 72 which are configured in the form of spike-like bone pins 74. Optionally, these can also have barb-like serrations. Preferably, the bone anchoring elements 72 are configured in one piece with the bone plate 66.

For coupling the screw shaft 26 with the bone alignment device 62, the coupling device 64 comprises first and second coupling elements 76 and 78 which are in force-locking and/or form-locking engagement when in the alignment position and are arranged or formed on the bone alignment device 62 on the one hand and the screw shaft 26 on the other.

The first coupling element 76 is configured in the form of a coupling projection 80 on the screw shaft 26, while the second coupling element 78 is configured in the form of a coupling receptacle 82, corresponding to the coupling projection 80, on the bone alignment device 62. As clearly shown in FIGS. 5 and 6 for example, the coupling projection 80 engages in the coupling receptacle 82 in a form-locking or essentially form-locking manner when in the alignment position.

In the exemplary embodiment of the pedicle screw system 20 as illustrated in the figures, the coupling projection 80 is formed by the annular flange 60. This can be formed in particular in one piece with the screw shaft 26. Alternatively, the coupling projection 80 can also be connected to the screw shaft 26 in a force-locking manner and/or with a substance-to-substance bond, such as by press-fitting, adhesive bonding, soldering or welding.

As clearly shown in the figures, the coupling projection 80 is arranged between the external thread 28 and the joint head 42. Moreover, an external diameter 84 of the coupling projection 80 is also larger than a maximum external diameter 86 of the external thread 28.

The coupling receptacle 82 is configured in the form of a recess 88 of the bone alignment device 62.

The bone alignment device 62 further comprises a screw shaft receptacle 90 through which the screw shaft extends when in the alignment position. It is configured in the form of a through-hole 92 of the bone plate 66. The coupling receptacle 82 is directly adjacent to the screw shaft receptacle 90.

An internal diameter 94 of the coupling receptacle 82 is larger than an internal diameter of the screw shaft receptacle 90. With the dimensions for the coupling receptacle 82 and of the screw shaft receptacle 90 thus chosen, a through-hole is formed which tapers in one step in a distal direction, said through-hole defining an annular face 98 pointing in a proximal direction and partially bounding the coupling receptacle 82, said annular face 98 having an annular face 100 of the annular flange 60 in contact, or stopping, thereagainst when in the alignment position, said annular face 100 pointing in a distal direction.

In the exemplary embodiment shown in the figures, the coupling device 64 defines a longitudinal axis 102 which runs parallel to or coincides with a screw shaft longitudinal axis 104 of the screw shaft 26.

Alternatively, it is also conceivable for a longitudinal axis of the coupling device 64 which is for example predetermined by a longitudinal axis 106 of the screw shaft receptacle 90 to be configured such that it is inclined by an angle of inclination 110 with respect to a longitudinal axis 108 which is predetermined by the coupling receptacle 82. The angle of inclination 110 can be a value in the range of approximately 0° to approximately 30°, for example.

Figure 2:
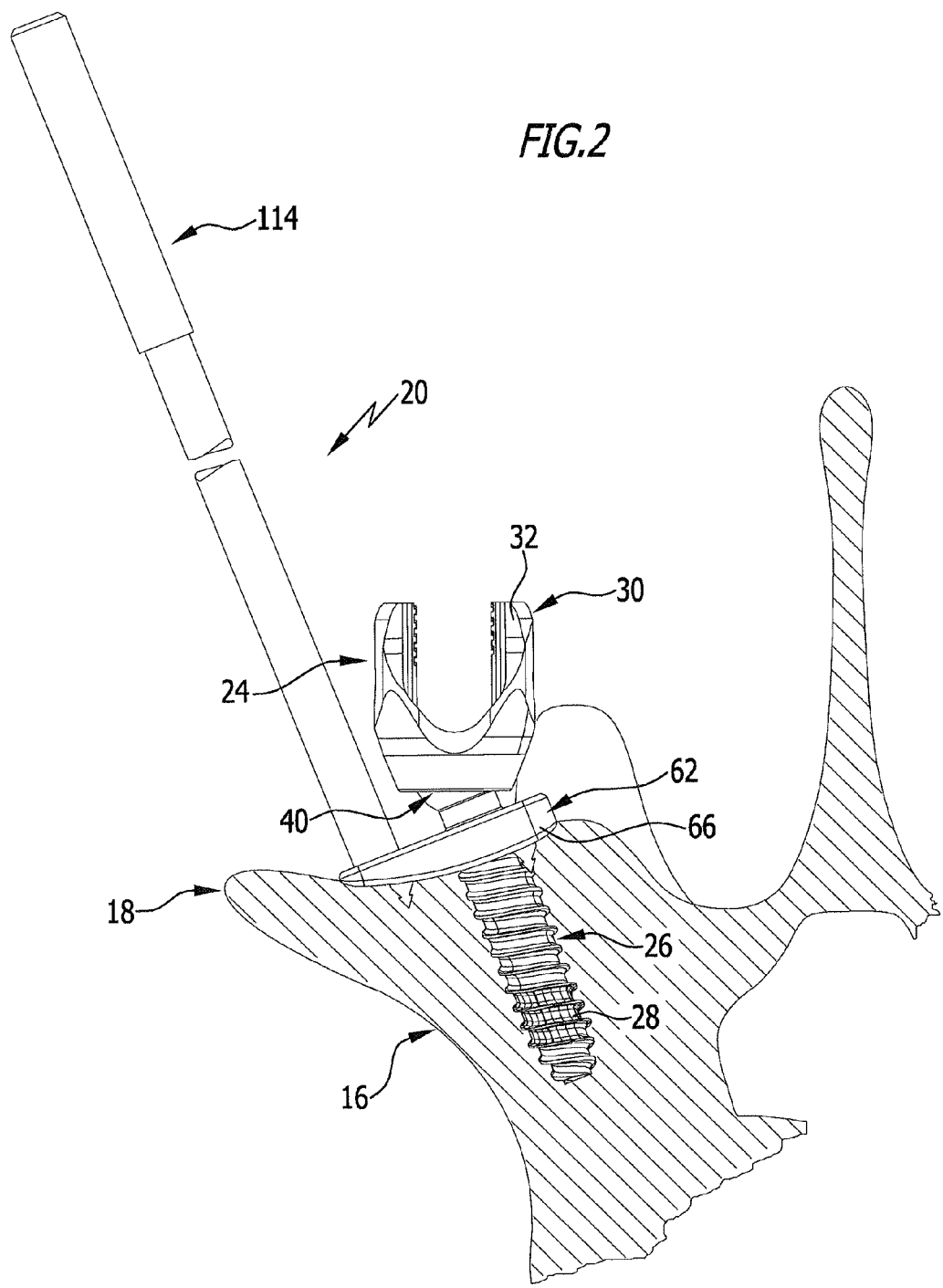
FIG. 2 is a side view of a pedicle screw system, shown as being screwed into a vertebra.
Figure 3:
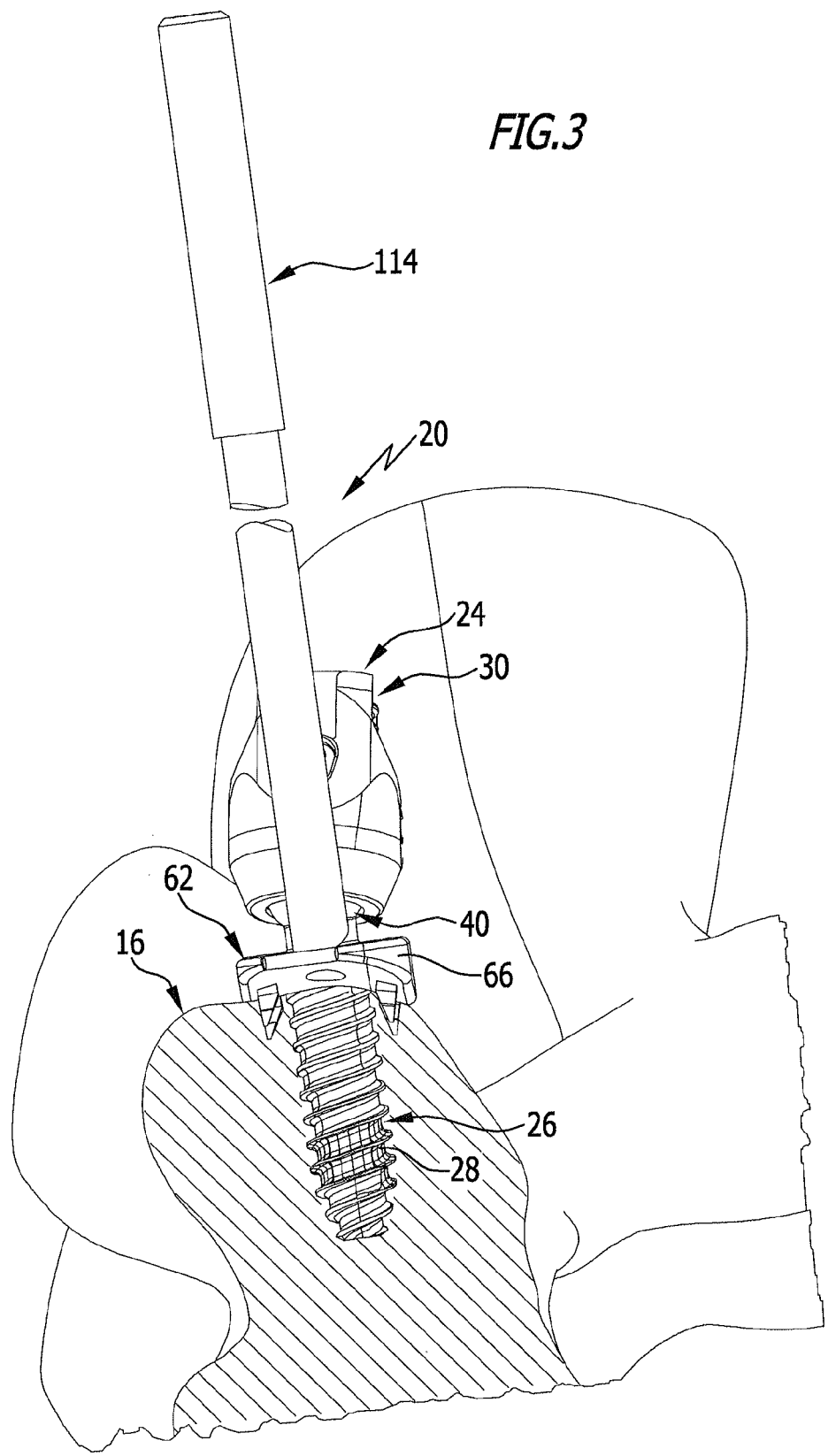
FIG. 3 is another side view of the pedicle screw system illustrated in FIG. 2.
Figure 4:
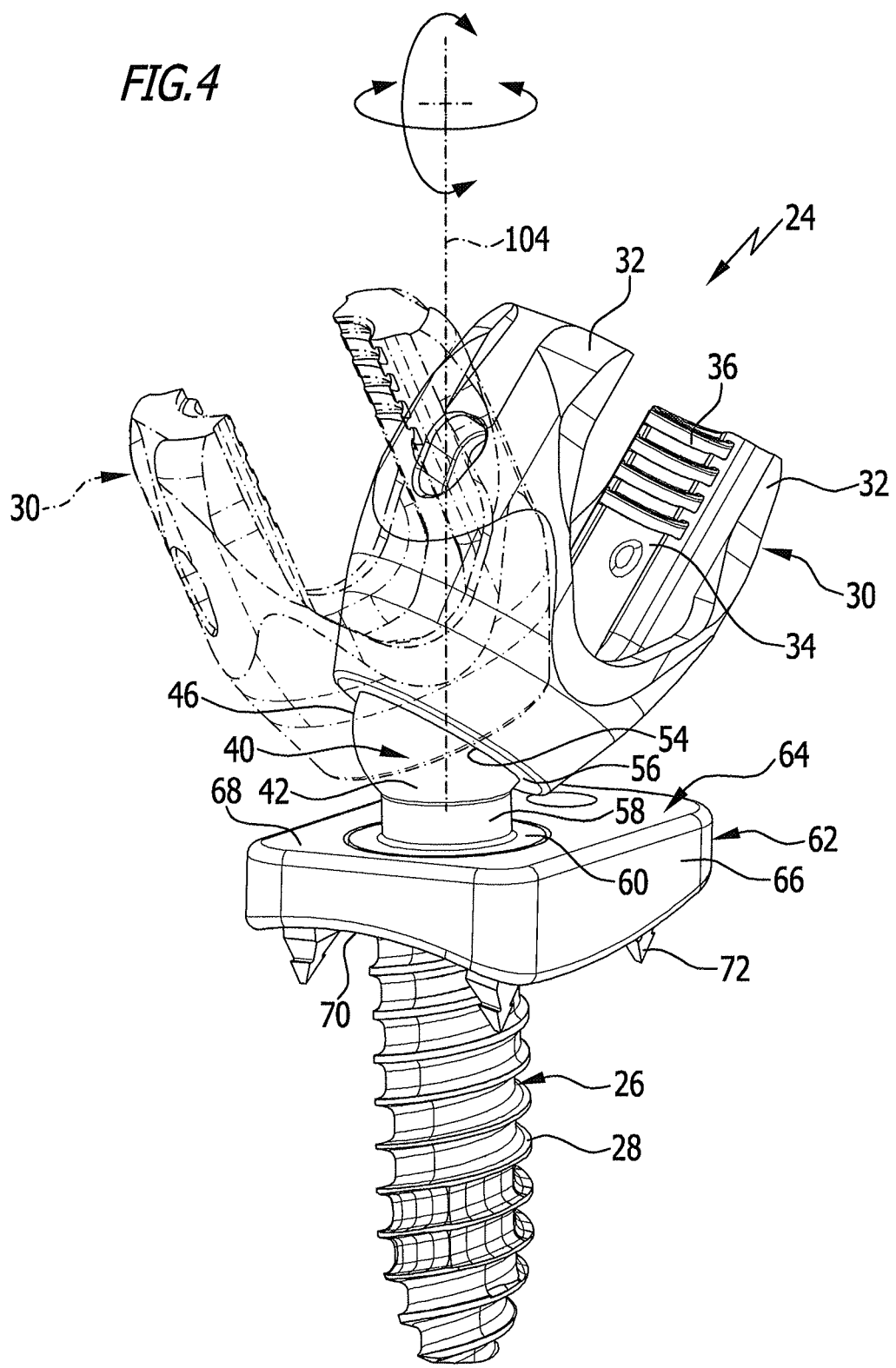
FIG. 4 is a schematic perspective view of the pedicle screw system of FIG. 2, comprising a pedicle screw having a bone alignment device coupled thereto.
Figure 5:
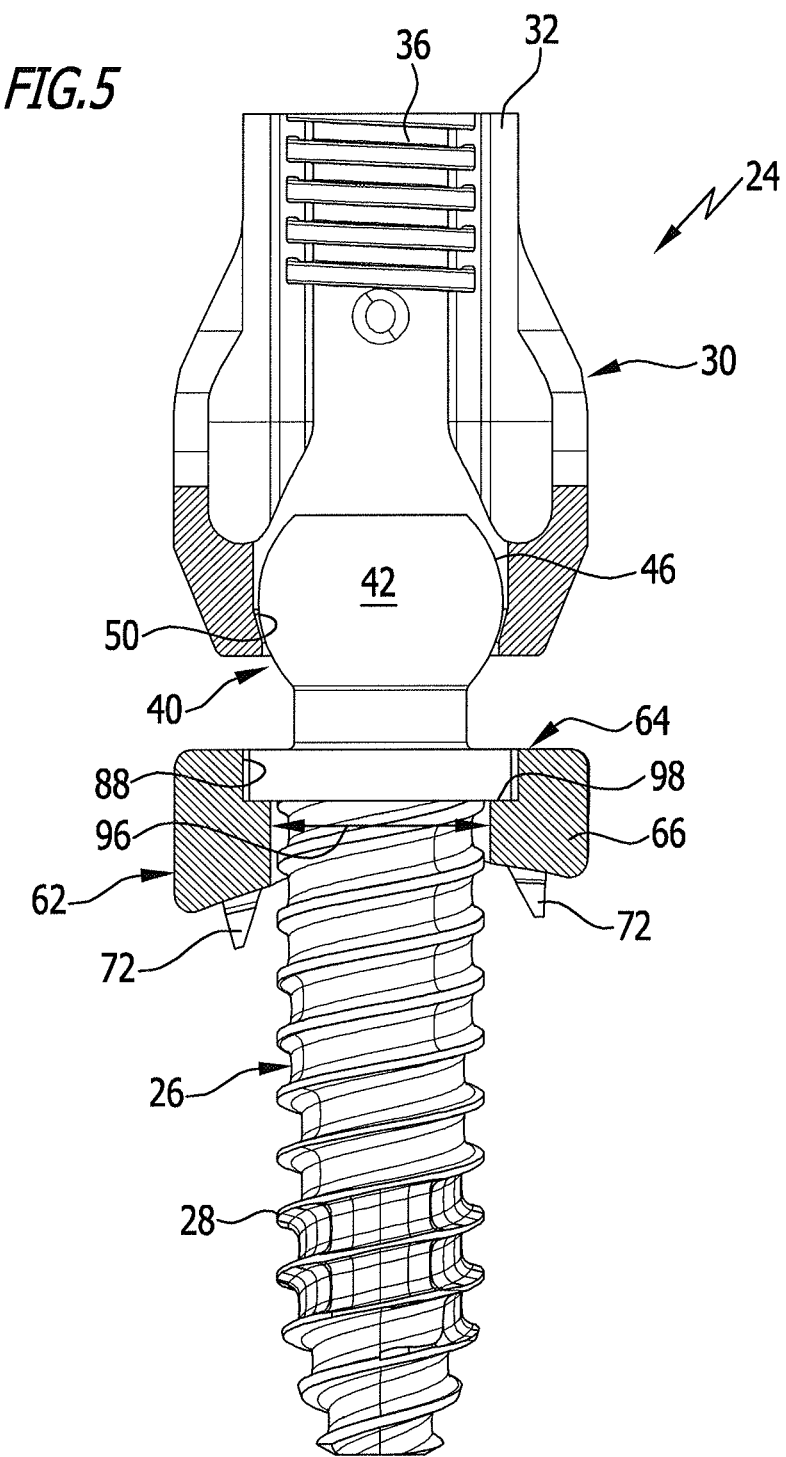
FIG. 5 is a side view of the pedicle screw system of FIG. 4, showing the bone alignment device and the screw head in section.
Figure 6:
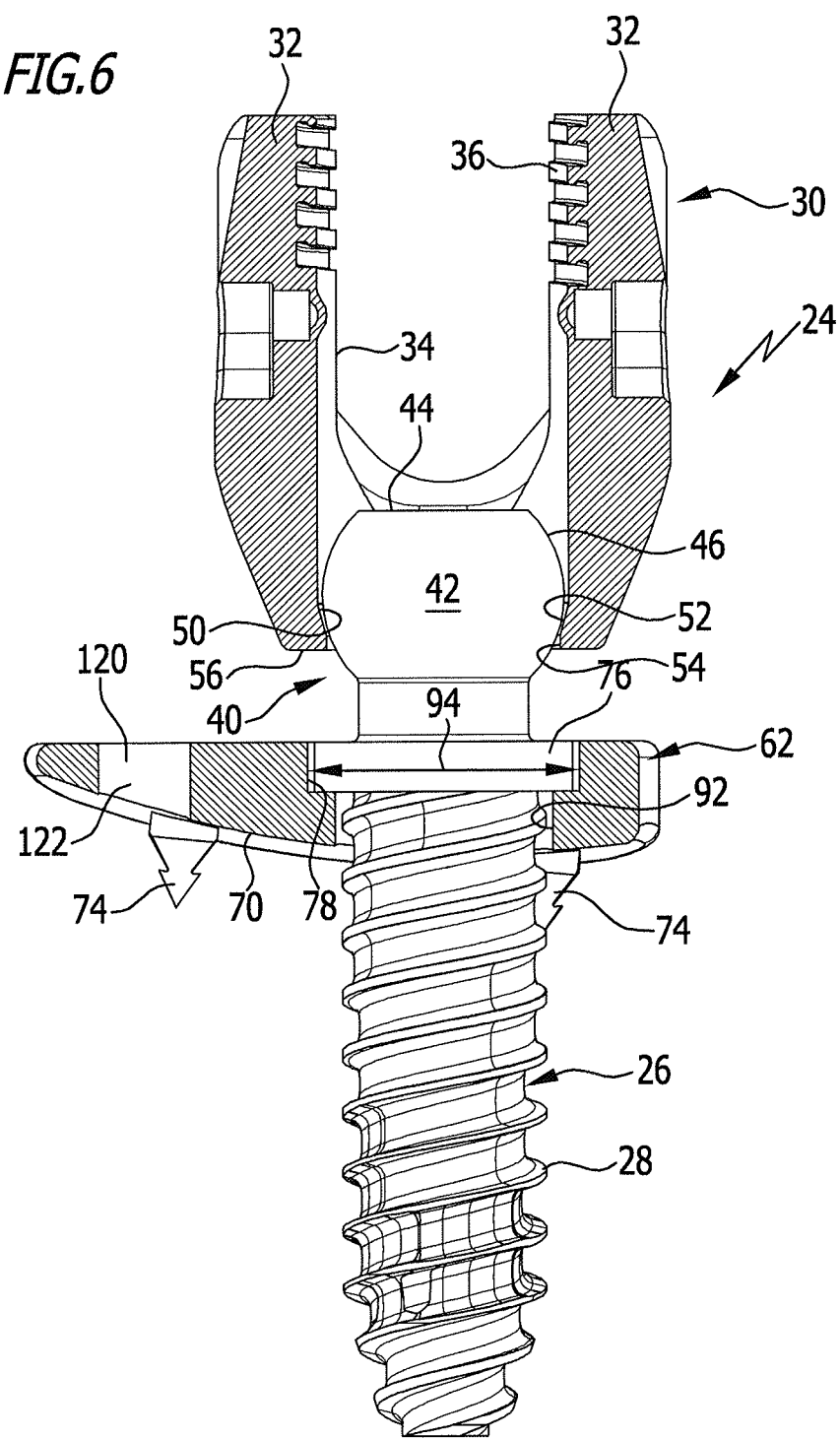
FIG. 6 is another side view of the pedicle screw system of FIG. 4, showing the bone alignment device and the screw head in section.
Figure 7:
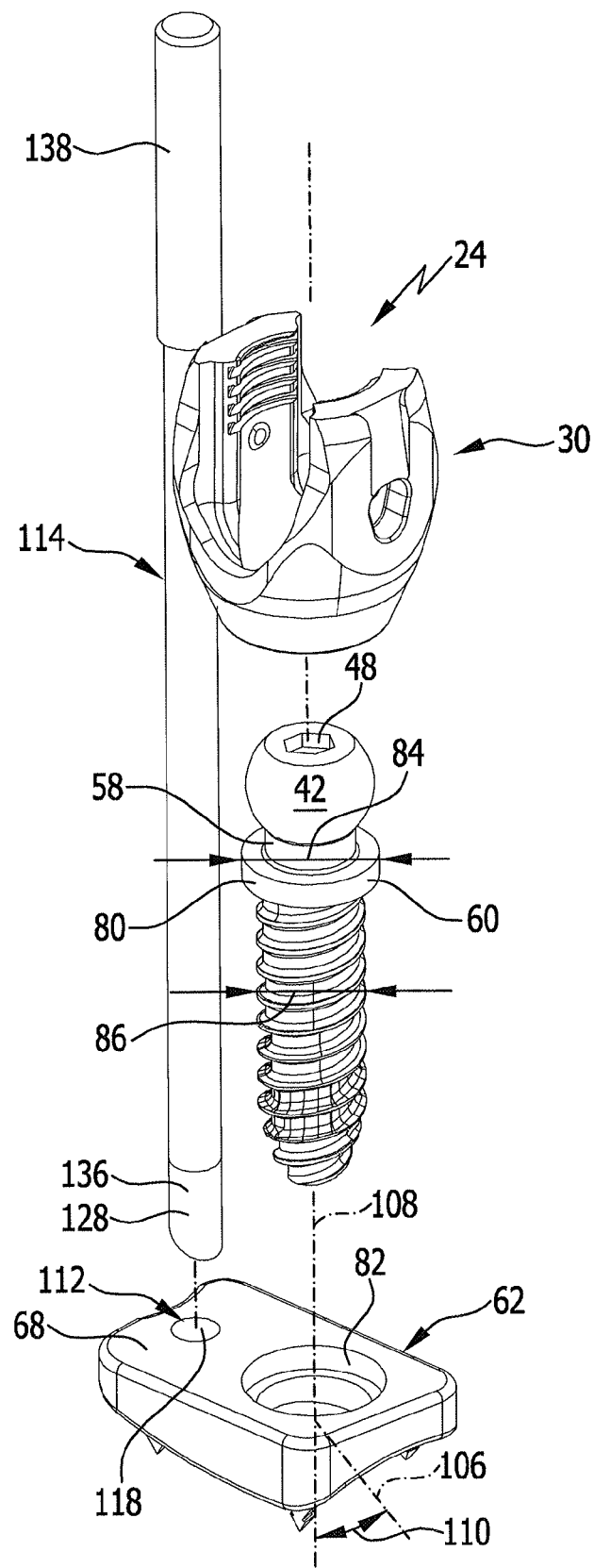
FIG. 7 is an exploded view of the pedicle screw system of FIG. 1 with an alignment instrument.
Figure 8:
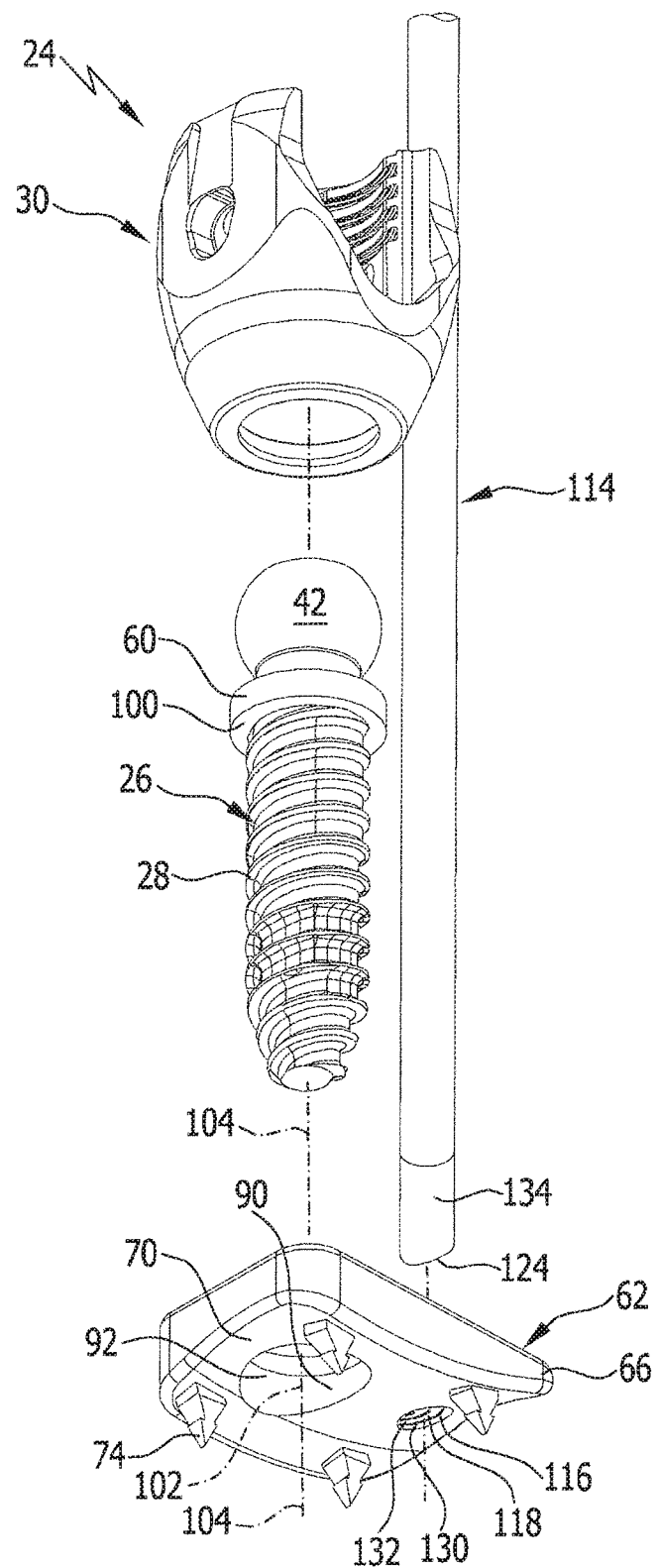
FIG. 8 is another exploded view in perspective of the pedicle screw system of FIG. 7.

Furthermore, the bone alignment device 62 preferably comprises at least one coupling device 112 for temporary force-locking and/or form-locking coupling with an alignment instrument 114 in a coupling position shown in FIGS. 2 and 3 for example.

The coupling device 112 comprises at least one coupling element 116 for force-locking and/or form-locking coupling with the alignment instrument 114 in the coupling position. In particular, the coupling element 116 may be configured in the form of a coupling projection or, as exemplified in the figures, in the form of a coupling recess 118. Furthermore, it is alternatively also possible to provide both a coupling projection and a coupling recess on the bone alignment device 62.

The coupling recess 118 in the exemplary embodiment shown in the figures is configured in the form of a through-hole 120 of the bone plate 66. Alternatively, it is also possible for the coupling recess 118 to be configured in the form of a blind hole. Preferably, the through-hole 120 is configured in the form of a bore 122.

In order to realize a simple and safe connection between the alignment instrument 114 and the bone alignment device 62, a coupling end 128 is formed, starting from a distal end 124 of the alignment instrument 114, for force-locking and/or form-locking coupling with the coupling device 112 of the bone alignment device 62. To this end, the coupling element 116 which is configured in the form of the bore 122 can be further provided with a thread 130, particularly an internal thread 132, or it can be configured in the form of a latch element. The coupling end 128 is then preferably configured in a manner corresponding to the coupling device 112, i.e. for example likewise in the form of a latch element or comprising a thread 134 in the form of an external thread 136.

The spinal stabilization system 10 and the pedicle screw systems 20 thereof work as described in the following.

For insertion of the pedicle screw 24 into the vertebra 16, the screw shaft 26 is screwed into the vertebra 16 using a screw-driving instrument, not shown in the figures, which has a tool end corresponding to the tool element receptacle 48. To this end, the vertebra can be provided with a pre-drilled hole or otherwise provided with a guide opening.

The bone alignment device 62 can already be coupled with the screw shaft 26 before the screw shaft 26 is screwed in so that the screw shaft 26 and the bone alignment device 62 will already assume the alignment position. It is alternatively conceivable to attach the bone plate 66 to a desired location on the vertebra 16, for example by tapping the bone anchoring elements 72 into the vertebra 16 with a mallet. The screw shaft 26 can then be screwed into the vertebra 16 through the coupling receptacle 82 and the screw shaft receptacle 90 until the annular flange 60 stops against the annular face 98 of the coupling receptacle 82.

In order to achieve safe orientation and fastening of the pedicle screw 24 to the vertebra 16, the alignment instrument 114 can optionally already be connected to the bone plate 66 in the above-described manner when the pedicle screw 24 is being screwed in by bringing the coupling end 128 and the coupling device 112 into force-locking and/or form-locking engagement with each other. A surgeon can thus grasp a proximal end of the alignment instrument 114, which is preferably configured in the form of a handle element 138, and thereby align and hold the bone plate 66 in a desired orientation.

Once the pedicle screw 24 has been anchored in the vertebra 16, as exemplified schematically in FIGS. 2 and 3, a surgeon can, by manipulating the alignment instrument 114, cause the vertebra 16 as a whole to be moved and brought into a desired position in order to bring the spine 18 back into an intended form.

Each of the pedicle screws 24 can be coupled, and at the same time moved, with an alignment instrument 114 in this way.

By having the screw heads 30 and the screw shafts 26 coupled via the ball-and-socket joint 40 in a ball-and-socket relationship with each other, it is then possible for the connecting element 14 to be inserted into the connecting element receptacles 34 and fixed in place therein by the fixation screws in a simple manner. Namely, the screw heads 30 can be pivoted relative to the screw shafts 26 about a midpoint of the joint head 42 and can be aligned such that for example a rod-shaped connecting element 14 can be placed into the connecting element receptacles 34 without further deformation of the pedicle screws 24.

The proposed pedicle screw system 20 thus combines, on the one hand, the advantages of a polyaxial screw with, on the other hand, the potential option of manipulating vertebrae into which the pedicle screw is screwed as, in particular, in the case of pedicle screws with screw heads arranged immovably on the screw shaft or in the case of monoaxial screws.

The invention claimed is:

1. A pedicle screw system comprising a pedicle screw having a screw shaft with an external thread and having a screw head supported on the screw shaft in a ball-and-socket joint relationship therewith, which screw head comprises a connecting element receptacle for a connecting element of a spinal stabilization system, said pedicle screw system further comprising a bone alignment device and a coupling device for form-locking coupling of the bone alignment device and the screw shaft when in an alignment position, wherein the coupling device is designed for allowing an axially fixed but rotatable connection to be established between the bone alignment device and the screw shaft with respect to a screw shaft longitudinal axis of the screw shaft.

2. The pedicle screw system in accordance with claim 1, wherein the bone alignment device has at least one coupling device for at least one of temporary force-locking coupling and temporary form-locking coupling with an alignment instrument in a coupling position.

3. The pedicle screw system in accordance with claim 2, wherein the coupling device has at least one coupling element for at least one of force-locking coupling and form-locking coupling with the alignment instrument in a coupling position.

4. The pedicle screw system in accordance with claim 3, wherein the at least one coupling element is configured in the form of at least one of a coupling projection and a coupling recess.

5. The pedicle screw system in accordance with claim 4, wherein the coupling recess is configured in the form of a blind hole or a through-hole.

6. The pedicle screw system in accordance with claim 3, wherein the at least one coupling element comprises a thread or is configured in the form of a latch element.

7. The pedicle screw system in accordance with claim 2, said pedicle screw system further comprising an alignment instrument for at least one of temporary force-locking coupling and temporary form-locking coupling with the coupling device.

8. The pedicle screw system in accordance with claim 7, wherein the alignment instrument comprises on the distal side thereof a coupling end for at least one of force-locking coupling and form-locking coupling with the coupling device.

9. The pedicle screw system in accordance with claim 8, wherein the coupling end is configured in the form of a latch element or comprises a thread which is of a configuration corresponding to that of the thread of the at least one coupling element.

10. The pedicle screw system in accordance with claim 1, wherein the coupling device comprises first and second coupling elements which are in at least one of force-locking engagement and form-locking engagement when in the alignment position and are arranged or formed on the bone alignment device on the one hand and the screw shaft on the other.

11. The pedicle screw system in accordance with claim 10, wherein the first coupling element is configured in the form of a coupling projection and wherein the second coupling element is configured in the form of a coupling receptacle corresponding to the coupling projection.

12. The pedicle screw system in accordance with claim 11, wherein at least one of the coupling projection engages in the coupling receptacle in a form-locking manner or in an essentially form-locking manner when in the alignment position
and
the coupling projection is configured in one piece with the screw shaft or is connected to the screw shaft in at least one of a force-locking manner and with a substance-to-substance bond, in particular by press-fitting, adhesive bonding, soldering or welding,
and
the coupling projection is configured in the form of an annular flange
and
the screw shaft has a joint head and wherein the screw head has a joint head receptacle corresponding to the joint head for forming a ball-and-socket joint in cooperation with the joint head.

13. The pedicle screw system in accordance with claim 12, wherein the coupling projection is arranged between the external thread and the joint head.

14. The pedicle screw system in accordance with claim 1, wherein the bone alignment device is configured in the form of a bone plate.

15. The pedicle screw system in accordance with claim 14, wherein the bone plate has a planar upper side and a concavo-convexly curved underside, said underside adapted to a contour of a pedicle.

16. The pedicle screw system in accordance with claim 1, wherein the bone alignment device carries or comprises at least one bone anchoring element.

17. The pedicle screw system in accordance with claim 16, wherein the at least one bone anchoring element is configured at least one of in the form of a bone pin or a bone tooth and in one piece with the bone alignment device.

18. The pedicle screw system in accordance with claim 1, wherein the bone alignment device comprises a screw shaft receptacle in which the screw shaft engages at least partially when in the alignment position.

19. The pedicle screw system in accordance with claim 18, wherein the screw shaft receptacle is configured in the form of a through-hole of the bone alignment device.

20. The pedicle screw system in accordance with claim 1, wherein the coupling device defines a longitudinal axis which runs parallel to the screw shaft longitudinal axis of the screw shaft, or encloses an angle of inclination with the screw shaft longitudinal axis of the screw shaft.

21. A spinal stabilization system comprising at least two bone screws and at least one connecting element fixable on the at least two bone screws, wherein at least one of the at least two bone screws is configured in the form of a pedicle screw system comprising a pedicle screw having a screw shaft with an external thread and having a screw head supported on the screw shaft in a ball-and-socket joint relationship therewith, which screw head comprises a connecting element receptacle for a connecting element of a spinal stabilization system, said pedicle screw system further comprising a bone alignment device and a coupling device for form-locking coupling of the bone alignment device and the screw shaft when in an alignment position, wherein the coupling device is designed for allowing an axially fixed but rotatable connection to be established between the bone alignment device and the screw shaft with respect to a screw shaft longitudinal axis of the screw shaft.

* * * * *